United States Patent
Gharib et al.

(10) Patent No.: US 8,197,234 B2
(45) Date of Patent: Jun. 12, 2012

(54) IN-LINE ACTUATOR FOR ELECTROMAGNETIC OPERATION

(75) Inventors: Morteza Gharib, San Marino, CA (US); Derek Rinderknecht, Pasadena, CA (US); Mladen Barbic, San Gabriel, CA (US)

(73) Assignee: California Institute of Technology, Pasadena, CA (US)

( * ) Notice: Subject to any disclaimer, the term of this patent is extended or adjusted under 35 U.S.C. 154(b) by 542 days.

(21) Appl. No.: 11/137,853

(22) Filed: May 24, 2005

(65) Prior Publication Data

US 2005/0275494 A1     Dec. 15, 2005

Related U.S. Application Data

(60) Provisional application No. 60/574,432, filed on May 25, 2004.

(51) Int. Cl.
  *F04B 43/08* (2006.01)
  *F04B 43/12* (2006.01)
  *F04B 45/06* (2006.01)

(52) U.S. Cl. ........ 417/474; 417/478; 417/322; 417/412; 417/410.1; 417/479

(58) Field of Classification Search .......... 417/474, 417/478, 322, 412; 92/91; 251/4, 65
See application file for complete search history.

(56) References Cited

U.S. PATENT DOCUMENTS

| | | | | |
|---|---|---|---|---|
| 3,511,583 A | * | 5/1970 | Brown | 417/412 |
| 3,593,718 A | * | 7/1971 | Krasner et al. | 607/20 |
| 3,768,931 A | * | 10/1973 | Willis, Jr. | 417/322 |
| 3,982,722 A | * | 9/1976 | Bernard | 251/4 |
| 4,463,502 A | * | 8/1984 | Fitzgerald et al. | 34/249 |
| 4,697,989 A | * | 10/1987 | Perlov et al. | 417/53 |
| 4,808,079 A | * | 2/1989 | Crowley et al. | 417/50 |
| 4,915,017 A | * | 4/1990 | Perlov | 92/5 R |
| 5,166,563 A | * | 11/1992 | Bassine | 310/15 |
| 5,203,172 A | * | 4/1993 | Simpson et al. | 60/545 |
| 5,394,132 A | * | 2/1995 | Poil | 335/232 |
| 5,996,964 A | * | 12/1999 | Ben-Shalom | 251/4 |
| 6,074,179 A | * | 6/2000 | Jokela et al. | 417/322 |
| 6,254,355 B1 | * | 7/2001 | Gharib | 417/53 |
| 6,278,847 B1 | | 8/2001 | Gharib et al. | |
| 6,408,878 B2 | * | 6/2002 | Unger et al. | 137/597 |
| 6,506,025 B1 | | 1/2003 | Gharib | |
| 6,580,503 B2 | | 6/2003 | Gharib et al. | |
| 6,582,208 B2 | | 6/2003 | Gharib | |
| 6,607,368 B1 | | 8/2003 | Ross et al. | |
| 6,608,668 B2 | | 8/2003 | Gharib et al. | |

(Continued)

FOREIGN PATENT DOCUMENTS

WO    WO 2004/048778    6/2004

(Continued)

*Primary Examiner* — Charles Freay
*Assistant Examiner* — Christopher Bobish
(74) *Attorney, Agent, or Firm* — Law Office of Scott C. Harris, Inc.

(57) ABSTRACT

An electromagnetic actuator for a microfluidic pump of the type that causes periodic pinching and releasing against the walls of a fluidic channel, e.g., a tube. At least one permanent magnet is placed against the walls of the fluidic channel, and located in an area with magnetic fields, produced by coils that are radially symmetric to the channel. The permanent magnet is cause to press and release against the wall of the fluid channel to cause a fluid flow through the channel.

17 Claims, 3 Drawing Sheets

U.S. PATENT DOCUMENTS

| | | |
|---|---|---|
| 6,679,687 B2 | 1/2004 | Gharib |
| 6,717,172 B2 | 4/2004 | Gharib et al. |
| 6,884,040 B2 * | 4/2005 | Dooley .......................... 417/53 |
| 6,910,466 B2 * | 6/2005 | Veinotte ........................ 123/520 |
| 6,956,230 B1 | 10/2005 | Gharib et al. |
| 7,006,132 B2 | 2/2006 | Pereira et al. |
| 7,033,132 B2 | 4/2006 | Gharib |
| 2001/0046445 A1 | 11/2001 | Gharib |
| 2002/0044867 A1 | 4/2002 | Gharib |
| 2002/0075474 A1 | 6/2002 | Gharib et al. |
| 2002/0113963 A1 | 8/2002 | Gharib et al. |
| 2002/0149691 A1 | 10/2002 | Pereira et al. |
| 2002/0162956 A1 | 11/2002 | Gharib et al. |
| 2003/0233143 A1 | 12/2003 | Gharib et al. |
| 2004/0101414 A1 | 5/2004 | Gharib et al. |
| 2004/0136846 A1 | 7/2004 | Gharib |
| 2004/0151607 A1 | 8/2004 | Gharib |
| 2004/0193035 A1 | 9/2004 | Gharib |
| 2005/0277865 A1 | 12/2005 | Gharib et al. |
| 2006/0195180 A1 | 8/2006 | Kheradvar et al. |
| 2006/0196642 A1 | 9/2006 | Gharib et al. |
| 2006/0209193 A1 | 9/2006 | Pereira et al. |
| 2006/0216173 A1 | 9/2006 | Kheradvar et al. |

FOREIGN PATENT DOCUMENTS

| | | |
|---|---|---|
| WO | WO 2005/115502 | 12/2005 |
| WO | WO 2005/117240 | 12/2005 |

\* cited by examiner

IN-LINE ACTUATOR FOR ELECTROMAGNETIC OPERATION

This application claims priority from provisional application No. 60/574,432, filed May 25, 2004, the contents of which are herein incorporated by reference.

BACKGROUND

U.S. Pat. Nos. 6,254,355 and 6,679,687 teach a microfluidic pump which uses compression of an area within a section of fluidic channel, in order to cause a fluid flow along the channel. This pump can be micro miniaturized, and can be made using micro machining techniques. Basically, an area of the channel is compressed in a certain way in order to cause fluid flow along the channel.

The above-discussed patents teach various ways of compressing of the channel.

SUMMARY

The present application describes an electromagnetic actuator that uses in-line coils to form the actuation for a microfluidic pump of a type that requires a portion of the channel to be compressed. According to the techniques disclosed herein, a magnetic field may be oriented along an axis of the channel, and used to carry out compression for actuating the pump.

BRIEF DESCRIPTION OF THE DRAWINGS

These and other aspects will now be described with reference to the accompanying drawings, wherein.

DETAILED DESCRIPTION

The embodiments disclosed herein use magnetic actuation of a microfluidic pump. These techniques form a moving magnetic field gradient that drives an actuator to compress the channel wall. In an embodiment, the channel is formed of a flexible tube. A ferromagnetic material, such as a permanent magnet, is coupled to the wall of the tube. The actuation arrangement can be made cylindrically symmetric, in order to facilitate miniaturization and symmetry.

According to an aspect, the interaction of the magnetic moment in a gradient magnetic field is used. This interaction force is described by the tensor relation:

$$\vec{F} = \nabla(\vec{m} \cdot \vec{B}) \tag{1}$$

Where the vector m represents the magnetic moment, and the vector B represents the magnetic field at the location of the magnetic moment.

Equation 1 can be expanded into three orthogonal force directions as follows:

$$F_x = m_x \frac{\partial B_x}{\partial x} + m_y \frac{\partial B_y}{\partial x} + m_z \frac{\partial B_z}{\partial x} \tag{2}$$

$$F_y = m_x \frac{\partial B_x}{\partial y} + m_y \frac{\partial B_y}{\partial y} + m_z \frac{\partial B_z}{\partial y} \tag{3}$$

$$F_z = m_x \frac{\partial B_x}{\partial z} + m_y \frac{\partial B_y}{\partial z} + m_z \frac{\partial B_z}{\partial z} \tag{4}$$

Which shows the relevant forces on the magnets, in the embodiments.

Figure 1:
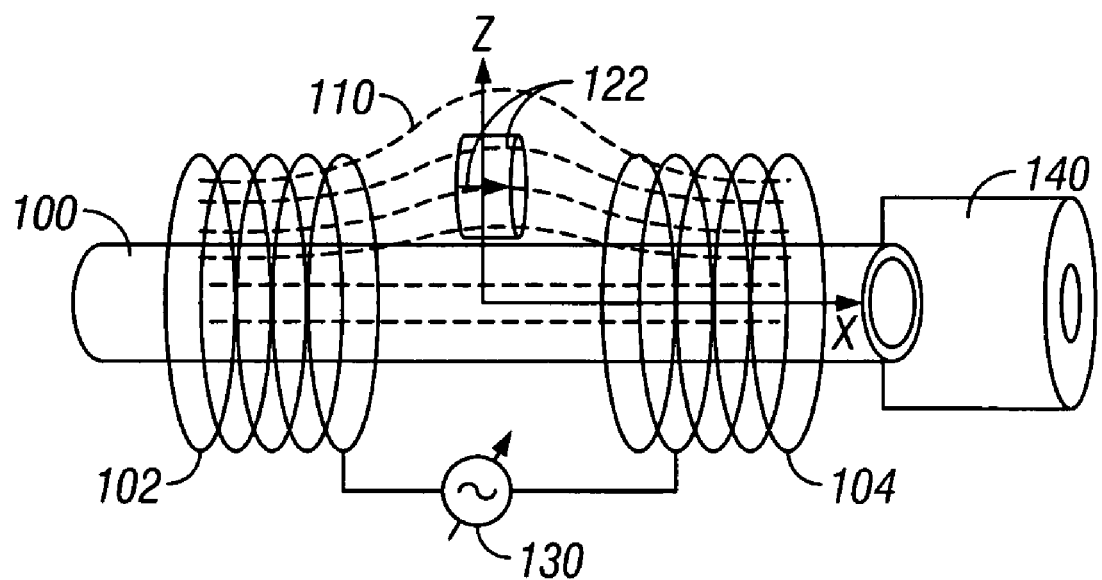
FIG. 1 shows an illustration of the tube based pump and the magnetic coils and actuator that actuate the pumping system.

FIG. 1 shows an embodiment. A tube 100 forms the element which will receive the pumping force. Another tube 140, having different fluidic characteristics, is attached to the first tube 100. More generally, however, the tubes 100, 140 can be any fluidic channels.

First and second coil sets 102, 104 are wound around the tube 100. The coils 102, 104 have electrical connections which allows their electrical actuation.

The coils may be wound azimuthally symmetrically along the x axis, shown as being along the tube 100 in FIG. 1. In an aspect, these coils may also be electrically connected to one another, so that their magnetic fields are energized in phase with one another. The coils form a symmetric magnetic field, which approximately follows the magnetic field lines 110 shown in FIG. 1. A magnetically effected part 122 is located with its magnetic field oriented parallel to the symmetric axis of the coils. In an embodiment, the effected part can be a permanent magnet whose magnetic field is in the x direction in FIG. 1. The permanent magnet element 122 may be substantially in the shape of a section of a cylinder, for example, but can be other shapes also. In an embodiment, the permanent magnet is radially symmetric.

The analytic expressions, using cylindrical coordinates, for the fields from a single coil turn of radius a along the radial, angular and z axes are well-known:

$$B_\phi = 0 \tag{5}$$

$$B_r = \frac{J}{c} \frac{2z}{r\sqrt{[(a+r)^2 + z^2]}} \left[ -K + \frac{a^2 + r^2 + z^2}{(a-r)^2 + z^2} E \right] \tag{6}$$

$$B_z = \frac{J}{c} \frac{2}{\sqrt{[(a+r)^2 + z^2]}} \left[ K + \frac{a^2 - r^2 - z^2}{(a-r)^2 + z^2} E \right] \tag{7}$$

where K and E are complete elliptic integrals of the first and second kind, respectively:

$$K = \int_0^{\frac{1}{2}\pi} \frac{d\theta}{\sqrt{(1 - k^2 \sin^2\theta)}} \text{ and} \tag{8}$$

$$E = \int_0^{\frac{1}{2}\pi} \sqrt{(1 - k^2 \sin^2\theta)}\, d\theta \text{ with} \tag{9}$$

$$k^2 = \frac{4ar}{[(a+r)^2 + z^2]} \tag{10}$$

These equations can be used to numerically evaluate the exact values of the magnetic fields and the field gradients for the coil configurations in FIG. 1.

In the embodiment, the magnet 120 is in contact with the outer surface of the fluidic channel. Magnetic moment is oriented along the X direction, so that the force on the magnet is in the z direction is:

$$F_z = m_x \frac{\partial B_x}{\partial z} \quad (11)$$

Figure 2:
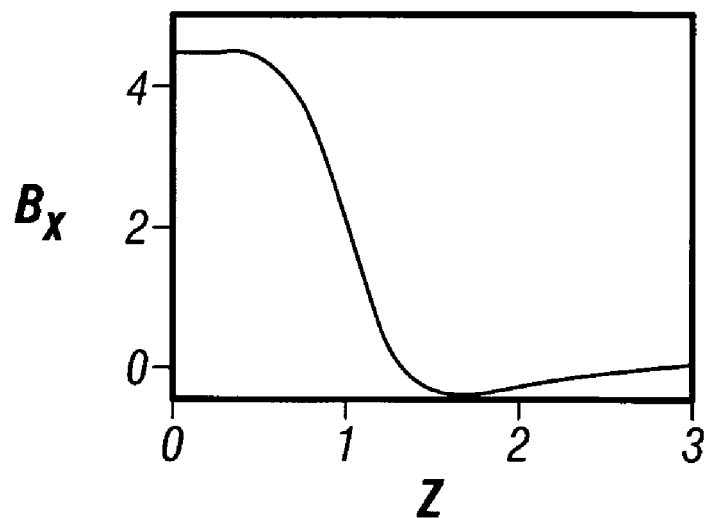
FIGS. 2 and 3 show characteristic curves of forces within the pump.
Figure 3:
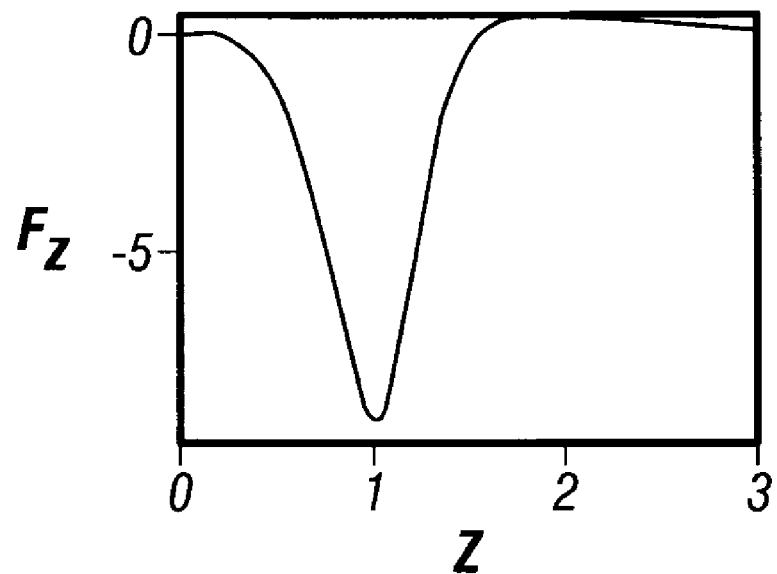

FIG. 2 shows a graph of the value of the x component of the magnetic field along the z axis, centered in between the two coils 102, 104. The force curve from equation 11, along the z axis is shown as the graph in FIG. 3. Note that the force curve has a distinct minimum, approximately at "1".

Passing an alternating current through the coils creates an alternating force on the magnet 120 along the z-axis direction. This alternating current may be tuned to the harmonic of the system, in order to maximize or modulate the pumping action. The magnet 120 can be attached to the outer surface in any desired way, for example by gluing or some other connection.

Figure 4:
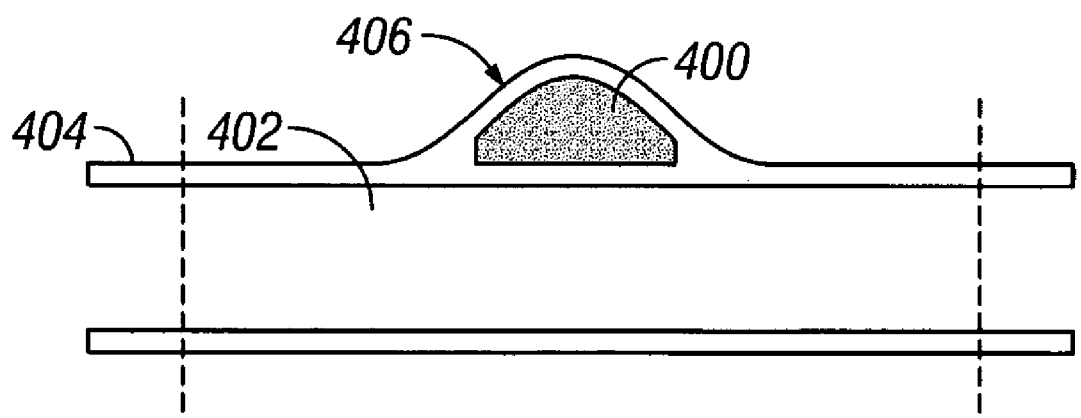
FIG. 4 illustrates the actuator being embedded within the elastic wall of a tube.

FIG. 4 shows an embodiment in which the permanent magnet element 400 is embedded within a wall of the fluidic channel. The fluidic channel 402 is shown with walls 404. The walls 404 include a pocket section therein at area 406. The permanent magnet element 400 is embedded in that pocket section. The permanent magnet element may take the form of a complete radial ring or any pattern formed by any section of the ring. This section can change the ring into an even or odd number of sections, and the individual sections may take on any geometry.

FIG. 4 shows a single magnet element 400.

Figure 5:
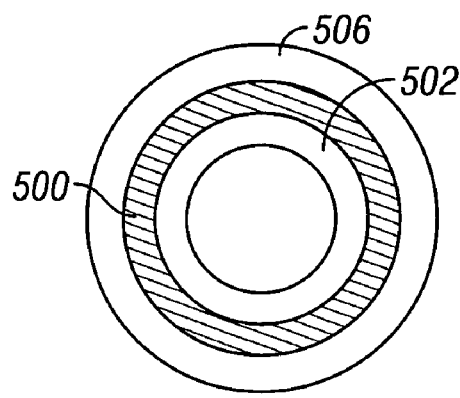
FIG. 5 illustrates the pumping actuator being encased and totally surrounding the tube's circumference.

FIG. 5 shows an embodiment with a complete ring of ferromagnetic material 500, formed between the inner wall 502 of the tube, and the outer wall 506. This may be any number of separate magnet pieces embedded in the tube wall. In the FIG. 5 embodiment, the magnet elements are cylindrically symmetrical.

Figure 6:
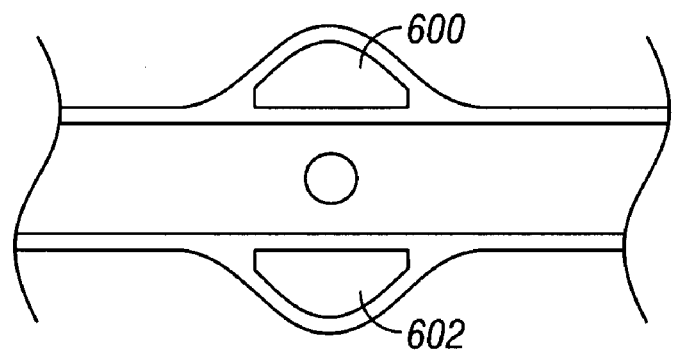
FIG. 6 illustrates the actuator being on opposite sides of the tube.

Another embodiment, shown in FIG. 6, has first magnet element 600, and an additional magnet element 602 at the opposite side of the tube.

The magnet elements may be formed of any ferromagnetic material, including, but not limited to, permalloy, NdFeB, AlNiCo and SmCo.

Figure 7:
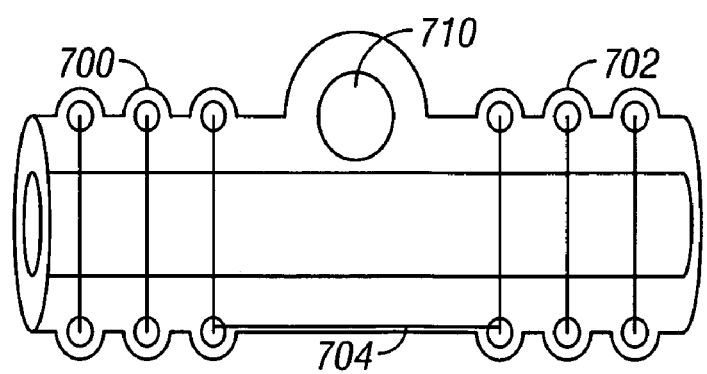
FIG. 7 illustrates an embodiment where both the actuator and the coils are encased within the tube wall.

In another embodiment shown in FIG. 7, the inductive coils 700, 702 are embedded within the elastic tube wall. A wire 704 may extend between the coils 700, 702. A single magnet 710 is shown; however, this may use any of the other configurations shown and described herein. This may form a more compact configuration where all of the parts are embedded in the tube.

In the embodiment, the pump may be comprised of an elastic section of tube, having a cross-sectional area of approximately 2.8 mm². This is connected to a rigid glass section with an area of approximately 0.5 mm². The elastic section of the pump is formed of silicon rubber, having a Young's modulus of about 220 kPa. Wave reflections are created by an impedance mismatch that is provided by asymmetric pinching with respect to the stiffer materials at the interfaces.

The coil receives an input waveform of a 50 Hz square wave, with 48 ma amplitude, and an offset of minus 24 ma. The coils may be energized by a variable power source, shown as 130 in FIG. 1. The frequency for the desired flow rate and flow direction is dependent on the properties of the materials that are used, the wall thickness, and the length of the segments. These properties can be calculated mathematically, or alternatively, the power supply and frequency generator can be variable, as shown, to enable experimental determination of the optimum properties.

Although only a few embodiments have been disclosed in detail above, other modifications are possible, and this disclosure is intended to cover all such modifications, and most particularly, any modification which might be predictable to a person having ordinary skill in the art. For example, while the above has described the fluidic channel as being a tube, it should be understood that any fluidic channel of any type can be used, so long as it is deformable in some way. Moreover, while the embodiment describes using the disclosed system for compressing a wall for a hydroelastic type pump, this system can be used for any application where a fluidic channel requires compression, for example it can be used to completely pinch of a channel for a valve, or to restrict a flow, e.g., as a variable flow restrictor. This can also be used for compressing a part within a peristaltic pump, for example.

Also, only those claims which use the words "means for" are intended to be interpreted under 35 USC 112, sixth paragraph. Moreover, no limitations from the specification are intended to be read into any claims, unless those limitations are expressly included in the claims.

What is claimed is:

1. An electromagnetic pump for pumping fluid, comprising:
    a wall defining a fluidic channel along a length of the fluidic channel, said wall having an outer surface, and an inner surface, where an area wholly enclosed within the inner surface defines the fluidic channel along an axis;
    at least one coil, which is outside said wall and which extends completely around the fluidic channel and which extends along only a portion of said fluidic channel; and
    an effected part, located in an area within a magnetic field of said coils to be moved by said magnetic field in an area of said fluidic channel, said effected part extending completely around said fluidic channel, and an entirety of said effected part is moved by said magnetic field of said coils to change a size of the fluidic channel completely around said fluidic channel, but in only said portion which is only part of said length of said fluidic channel where said effected part is located, wherein said effected part is at least one permanent magnet material that is located embedded within said wall in an area of said wall that is completely between said outer surface and said inner surface, and where no part of said permanent magnet extends into the fluidic channel, and where no part of said the fluidic channel, other than said portion, is effected by the actuation of said effected part; and
    a controller for controlling a movement of said effected part, by causing periodic pinching of said effected part at a frequency that is based on a desired flow rate for pumping and where the frequency of pumping is controlled to create wave reflections in the fluid.

2. The pump as in claim 1, wherein said coil includes a first coil part and a second coil part, both said first and second coil parts being cylindrically symmetric to the fluidic channel.

3. The pump as in claim 2, further comprising an electrical connection between said first and second coil parts.

4. The pump as in claim 1, further comprising a connection to a source of power that drives said at least one coil.

5. The pump as in claim 4, wherein said source of power drives said at least one coil with an alternating current, and further comprises a device which adjusts at least one parameter of said alternating current.

6. The pump as in claim 5, wherein said at least one parameter is a frequency of said alternating current.

7. The pump as in claim 1, wherein said fluidic channel is a channel with a first fluidic characteristic, further comprising a second channel with a second fluidic characteristic, coupled to said fluidic channel, forming a pumping mechanism.

8. A method of pumping fluid through a channel, comprising:
    forming a magnetic field along an axis defined by a fluidic channel with a wall defining the fluidic channel, said forming being carried out from outside said fluidic channel, said wall having an outer surface, and an inner surface, where an area wholly enclosed within the inner surface defines the fluidic channel, said magnetic field defined by lines of force that extend along said the axis, and where the fluidic channel extends along a length;
    using said magnetic field to move a magnetic field effected part that effects said fluidic channel, wherein said forming the magnetic field comprises embedding permanent magnetic material into walls of the fluidic channel in an area of said wall that is completely between said outer surface and said inner surface, and where no part of said magnetic material extend into the fluidic channel, and where said magnetic material completely surround said fluidic channel and collectively cause a change in a size of said fluidic channel in only a single location along said length, where that single location is always the same location along said length which is less than entire length, and said fluidic channel is changed in only said single location that is only part of the length of the fluidic channel, wherein said forming a magnetic field comprises using a first and a second coil part that each completely surround said fluidic channel, and that extend along said axis and are separated from one another along said axis, with a first coil part in a first location relative to said axis, surrounding said fluidic channel at said first location, and said second coil part at a second location relative to said axis, surrounding said fluidic channel at said second location, where the effected part is between said first and second coil parts in an area that separates said first and second coil parts;
    controlling a movement of said effected part, by causing periodic pinching of said effected part at a frequency and where the frequency of pumping is controlling to create wave reflections in the fluid.

9. A method as in claim 8, wherein said using the magnetic field comprises embedding at least one permanent magnet as said magnetic elements into walls that define the fluidic channel.

10. A method as in claim 8, wherein there is a wire extending between said coil parts.

11. A method as in claim 8, further comprising electrically connecting said first and second coil parts using a wire that extends within said wall of said fluidic channel.

12. A method as in claim 8, further comprising driving the first and second coil parts in phase with one another.

13. A method as in claim 8, further comprising using movement of the magnetic field effected part to pump a fluid.

14. A method as in claim 8, further comprising electrically connecting said first and second coil parts using a wire that extends within said wall of said fluidic channel.

15. A pumping system, comprising:
    a first fluidic channel having first properties, said fluidic channel having an outer surface, and an inner surface, where an area wholly enclosed within the inner surface defines the first fluidic channel;
    a second fluidic channel, coupled to the first fluidic channel, and having second properties different than the first properties; and
    an actuator, on said first fluidic channel, having coil parts which are radially symmetric to the first fluidic channel, and having a magnetic effected part formed within an area of a magnetic field of said coil parts, said magnetic effected part including a permanent magnet material, and operating to compress the first fluidic channel to thereby cause fluid in the first fluidic channel to be pumped relative to the second fluidic channel, wherein said magnetic effected part is embedded within a wall of the first fluidic channel in an area of said wall that is completely between said outer surface and said inner surface, and where no part of said magnetic effected part extends into the fluidic channel, and where said magnetic effected part causes a change of size of the fluidic channel in only a single location along said first fluidic channel where said magnetic effected part is located, and less than a complete length of said first fluidic channel where that single location is always the same location, and where said effected part extending completely around said fluidic channel, and an entirety of said effected part is moved by said magnetic field of said coils to change a size of the fluidic channel completely around said fluidic channel; and
    a controller for controlling a movement of said effected part, by causing periodic pinching of said effected part at a frequency and where the frequency of pumping is controlled to create wave reflections in the fluid.

16. A pumping system as in claim 15, wherein said coil parts are embedded within a wall of the first fluidic channel in an area of said wall that is completely between said outer surface and said inner surface.

17. A pumping system as in claim 16, wherein there are two sets of inductive coils, spaced from one another and both embedded in the said wall between said inner surface and said outer surface, and a wire extending between said inductive coils, said wire extending between said inductive coils, said wire extending between said inductive coils wherein said forming a magnetic field comprises using coil parts that are cylindrically symmetrical to the fluidic channel.

* * * * *